United States Patent [19]

Jung et al.

[11] Patent Number: 4,714,724

[45] Date of Patent: Dec. 22, 1987

[54] DIBROMONEOPENTYL PHOSPHATE MELAMINE SALT FLAME RETARDANT

[75] Inventors: Alfred K. Jung, Ridgewood; Joseph Silberberg, Brooklyn; Edward D. Weil, Hastings-on-Hudson, all of N.Y.

[73] Assignee: Stauffer Chemical Company, Westport, Conn.

[21] Appl. No.: 426,562

[22] Filed: Sep. 29, 1982

Related U.S. Application Data

[62] Division of Ser. No. 146,583, May 5, 1980, Pat. No. 4,373,103.

[51] Int. Cl.$^4$ .................................................. C08K 5/34
[52] U.S. Cl. .................................................... 524/100
[58] Field of Search ........................................ 524/100

[56] References Cited

U.S. PATENT DOCUMENTS

| | | | |
|---|---|---|---|
| 3,887,655 | 6/1975 | Shim | 558/84 |
| 4,061,605 | 12/1977 | Simon | 521/108 |
| 4,080,501 | 3/1978 | Leman et al. | 544/195 |
| 4,365,033 | 12/1982 | Halpern et al. | 524/118 |
| 4,373,103 | 2/1983 | Jung et al. | 544/195 |

Primary Examiner—Morton Foelak
Assistant Examiner—Kriellion Morgan

[57] ABSTRACT

Dibromoneopentyl phosphate melamine salt is a novel flame retardant suitable for plastics, textiles and fabric backcoatings. The dibromoneopentyl phosphate melamine salt is prepared by the reaction of dibromoneopentyl phosphoric acid with melamine.

2 Claims, No Drawings

DIBROMONEOPENTYL PHOSPHATE MELAMINE SALT FLAME RETARDANT

This is a division of application Ser. No. 146,583 filed May 5, 1980, now U.S. Pat. No. 4,373,103.

BACKGROUND OF THE INVENTION

Compounds containing halogen are among those effective for imparting flame resistance to flammable substrates. In particular, many organic bromine compounds are known agents for compounding flame retardant plastics.

Phosphorus containing compounds also have utility for imparting flame resistance. For example, melamine, phosphate and salts of benzenephosphonic acid and melamine have been suggested as flame retardants (see, U.S. Pat. Nos. 4,061,605 and 4,080,501).

Phosphoramidate esters of dibromoeopentyl glycol useful as flame retardants for polymeric materials have been prepared (see, U.S. Pat. No. 3,887,655).

The requirements for a suitable flame retardant extend beyond the sole ability to impart flame resistance. A flame retardant suitable for plastics must be highly compatible with its base material not only under conditions of use but at the processing stage where the plastic and flame retardant are being compounded.

The environment of temperature and shear forces present in modern plastic milling equipment render some flame retardant compounds unsuitable because of instability, volatility, or a tendency to separate from the base plastic during compounding. The result is often a nonhomogenous product with unacceptable flame retardant characteristics.

It is desirable to develop new flame retardant agents which are effective, stable, and easily compounded into plastic materials with high temperature processing equipment.

THE INVENTION

Dibromoneopentyl phosphate melamine salt is a novel flame retardant agent.

Another aspect of this invention is a method of making dibromoneopentyl phosphate melamine salt by the reaction of melamine and dibromoneopentyl phosphoric acid.

Another aspect of this invention is a plastic composition containing a flame retardant effective amount of the dibromoneopentyl phosphate melamine salt.

Still another aspect of this invention is a textile backcoated or containing therein a flame retardant effective amount of the dibromoneopentyl phosphate melamine salt.

DETAILED DESCRIPTION OF THE INVENTION

The flame retardant composition of this invention designated, "dibromoneopentyl phosphate melamine salt" is a white solid substantially insoluble in water, polar, and non-polar organic solvents and having a decomposition point of approximately 300° C.

The dibromoneopentyl phosphate melamine salt of this invention is believed to be represented by the formula:

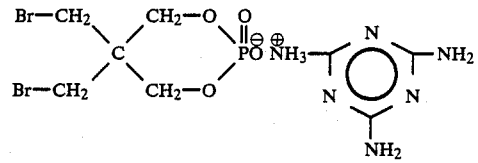

Dibromoneopentyl phosphate melamine salt is synthesized by reacting dibromoneopentyl phosphoric acid (i.e., the cyclic monobasic ester of dibromoneopentyl glycol and phosphoric acid) with melamine. The dibromoneopentyl phosphoric acid reactant may be prepared from a variety of sources such as hydrolysis of dibromoneopentyl phosphoric halides. The dibromoneopentyl phosphoric halides may in turn be prepared by the reaction of dibromoneopentylene glycol and phosphorus oxyhalide.

One possible reaction scheme is shown by the following chemical equation:

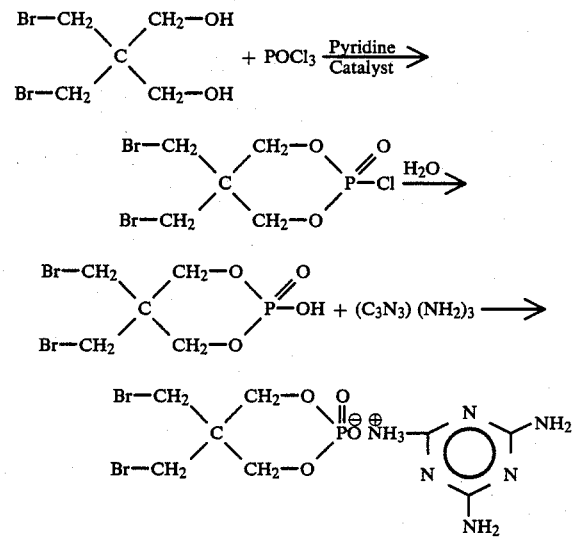

Alternatively, the dibromoneopentyl phosphoric acid may be prepared by the reaction of dibromoneopentyl glycol with $P_2O_5$ or phosphoric acid.

Preparation of dibromoneopentyl phosphate melamine salt in substantially quantitative yield is accomplished by reacting melamine with dibromoneopentyl phosphoric acid in a liquid reaction medium. The reaction medium should be a non-reactive liquid capable of dispersing or dissolving the reactants. Suitable reaction media include water, alcohols, chlorinated solvents, etc. Solid melamine reactant is dispersed in the liquid reaction medium in a ratio of approximately one mole of melamine per mole of dibromoneopentyl phosphoric acid (stoichiometric amounts) to yield a precipitate of dibromoneopentyl phosphoric acid product.

The order of addition of the reactants is not critical to the formation of the product. If desired, the reactants may be combined in other than stoichiometric proportions.

Reaction temperatures from about 0° C. to the boiling point of the reaction medium are suitable, although generally reaction temperatures from about 10° C. to about 180° C. are employed. Since the reaction product is generally substantially insoluble in the reaction medium, it may be conveniently separated by conventional processes such as filtration, decantation, centrifugation, or vaporization of the reaction medium. After separation, the product may be dried and ground to a particle size suitable for final use.

The reaction product of melamine and dibromoneopentyl phosphoric acid is generally suitable for use as a flame retardant without further purification.

The novel melamine salt composition of this invention may be employed to impart flame retardance to a wide variety of flammable substrates. Examples of such substrates are cellulosic materials, textiles, plastics, fabric backcoatings, foams, etc. The melamine salt flame retardant may be applied in flame retardant effective amounts (viz., generally about 5 to about 30 weight percent flame retardant based on the weight of flame retardant plus substrate) to flammable substrates by means such as padding, dipping, or spraying. The flame retardant may take the form of a powder, suspension, emulsion, or melt. The melamine salt composition may be chemically bound to the substrate or mechanically incorporated by conventional means such as a resin binder.

It is a preferred practice of this invention to use the dibromoneopentyl phosphate melamine salt as a flame retardant for plastics.

Examples of plastics which may be formulated with melamine salt of this invention are styrenic plastics such as polystyrene; polyamides such as nylon; polyesters such as polybutylene terephthalate; polyolefins such as polybutadiene, polypropylene, polyethylene, vinylchloride polymers, vinylchloride copolymers; and polyacrylates such as polymethacrylate.

Polyolefins are the most preferred materials for formulation with the flame retardants of this invention.

Typically, the dibromoneopentyl phosphate melamine salt is added to a plastic formulation in amounts sufficient to provide from about 5 to about 30 weight percent of the total weight of the formulated plastic.

The dibromoneopentyl phosphate melamine salt may be used as substantially the sole source of bromine in a flame retardant composition added to a substrate. Optionally, the flame retardant of this invention may be used in combination with any other known flame retardants, particularly organic bromine or phosphorus compounds having flame retardant utility. Nevertheless, the benefits of arising from the practice of this invention generally require that approximately at least one-half of the bromine content of a desired flame retardant formulation originate from the inclusion of the dibromoneopentyl phosphate melamine salt of this invention.

Examples of flame retardants and smoke suppressants which may be included in formulations containing the melamine salts of this invention are decabromodiphenyl oxide, bis(pentabromophenoxy)ethane, bis(tetrabromophthalimide)ethane, tetrabromobisphenol A, hexabromocyclododecane, bis(tribromophenoxy)ethane, octabromodiphenyl oxide, molybdenum oxide and molybdates, zinc oxide and zinc salts, magnesium oxide and carbonate, and alumina trihydrate.

EXAMPLE I

This Example illustrates the preparation of dibromoneopentyl chlorophosphate reactant represented by the formula:

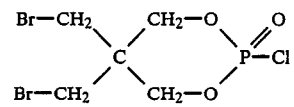

A three liter, three neck flask containing 500 ml. of chloroform was fitted with a reflux condenser, stirrer, thermometer and nitrogen inlet. Dibromoneopentylene glycol (0.75 moles) and $POCl_3$ (0.75 moles) were added to the flask with two milliliters of pyridine. The contents of the flask were heated at 65° C. for approximately five hours.

The reaction product was a solution of dibromoneopentylene chlorophosphate.

EXAMPLE II

One-half mole of dibromoneopentyl chlorophosphate was added with stirring to one liter of water. After approximately fifteen minutes, the solution became clear. To this solution was added 0.5 moles of melamine. The mixture was stirred for two and one-half hours, cooled in an ice bath, vacuum filtered, and oven dried for 45 hours.

The broad $P=O$ infrared band at about 1250–1280 $cm^{-1}$ characteristic of the $P=O$ (OH) structure in the starting acid, was absent from the infrared spectrum of the product salt; instead, the salt showed a band at 1222 $cm^{-1}$ not present in the spectrum of the acid. Likewise, the product infrared spectrum did not show a band at 3130 $cm^{-1}$ which occurs in the spectrum of unreacted melamine.

The precipitate product was approximately a stoichiometric yield of dibromoneopentyl phosphate melamine salt.

EXAMPLE III

This Example illustrates the use of dibromoneopentyl phosphate melamine salt composition as a flame retardant in polyolefin compositions.

Polypropylene (general purpose—Hercules 6523) mixed with 30 weight percent dibromoneopentyl phosphate melamine salt was fluxed on a 2-roll 15.24 cm. by 33.02 cm. Laboratory Mill (product of Farrell Mfg. Co.).

The mill was operated at a front roll temperature of 193° C. at 40 revolutions per minute and a back roll temperature of 165.5° C. at 30 revolutions per minute. The milling was continued for seven minutes after banding of the plastic on the roll.

The plastic formulation was removed from the mill and pressed at 190° C. into 0.3175 cm. thick plaques suitable for preparing test specimens.

Sample Evaluations:

The plastic composition prepared in this Example was evaluated for flame retardancy by the UL-94 Standard for Tests for Flammability of Plastic Materials for Parts in Devices and Appliances (Underwriters Laboratories, Inc., second edition as revised February 1975). The UL-94 test procedure is incorporated herein by reference.

The Table displays the pertinent data and the UL-94 Flammability Test results for the sample prepared by this Example.

TABLE

| Sample and Base Polymer | Flame Retardant Additive (wt. %) | UL-94 BURN CRITERIA NUMBER OF FLAME APPLICATIONS | | | UL-94 Rating |
| --- | --- | --- | --- | --- | --- |
| | | less than 10 sec. | Drip and ignite cotton | Total Burn Time (sec.) | |
| EX. II Polypropylene | Dibromoneopentyl Phosphate Melamine Salt (30) | 10 | 0 | 4 | V-O |

Test Results:

The dibromoneopentyl phosphate melamine salt composition of this invention is an effective flame retardant additive in polyolefin formulations. A notable amount of other formation occurred during the burn tests.

Although the invention has been described with respect to certain preferred embodiments, it should be understood that modifications obvious to one having ordinary skill of the art may be made without deviating from the scope of the invention which is defined by the following claims.

We claim:

1. A composition comprising a normally flammable polymer of styrene and a minor proportion, sufficient to impart flame-retardant properties to said compositions, of a salt of 5,5-bis(bromomethyl)-2-hydroxy-2-oxo-1,3,2-dioxaphosphorinane having the structure

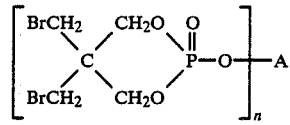

where A is a protonated amino-s-triazine group and n is an integer corresponding to the valence of A.

2. A composition comprising normally flammable polystyrene and a minor proportion, sufficient to import flame-retardant properties to said compositions, of a salt of 5,5-bis(bromomethyl)-2-hydroxy-2-oxo-1,3,2-dioxaphosphorinane having the structure

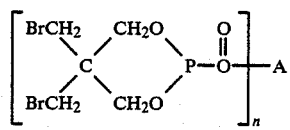

where A is a protonated amino-s-triazine group and n is an integer corresponding to the valence of A.

* * * * *

UNITED STATES PATENT AND TRADEMARK OFFICE
CERTIFICATE OF CORRECTION

PATENT NO. : 4,714,724
DATED : Dec. 22, 1987
INVENTOR(S) : Alfred K. Jung et al.

It is certified that error appears in the above—identified patent and that said Letters Patent is hereby corrected as shown below:

Col. 5, line 15, "other" should be --char--; and

Col. 6, line 15, "import" should be --impart--.

Signed and Sealed this

Seventeenth Day of May, 1988

Attest:

DONALD J. QUIGG

*Attesting Officer*         *Commissioner of Patents and Trademarks*